(12) United States Patent
Zeller et al.

(10) Patent No.: US 6,963,014 B1
(45) Date of Patent: Nov. 8, 2005

(54) $C_{13}$ ALCOHOL MIXTURE AND FUNCTIONALISED $C_{13}$ ALCOHOL MIXTURE

(75) Inventors: Edgar Zeller, Mannheim (DE); Marc Walter, Frankenthal (FR); Wolfgang Richter, Wachenheim (DE); Klaus Diehl, Hassloch (DE); Michael Röper, Wachenheim (DE); Jürgen Tropsch, Römerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/129,980

(22) PCT Filed: Nov. 17, 2000

(86) PCT No.: PCT/EP00/11440

§ 371 (c)(1),
(2), (4) Date: May 13, 2002

(87) PCT Pub. No.: WO01/36356

PCT Pub. Date: May 25, 2001

(30) Foreign Application Priority Data

Nov. 18, 1999 (DE) .......................................... 199 55 593

(51) Int. Cl.$^7$ .......................... C07C 27/20; C07C 27/22; C07C 27/24; C07C 29/15
(52) U.S. Cl. ........................................................ 568/909
(58) Field of Search .............................. 568/909, 8, 9, 568/10, 12, 18, 38, 75, 606, 613, 618; 536/1.11, 4.1, 18.5, 18.6

(56) References Cited

U.S. PATENT DOCUMENTS 5,849,972 A 12/1998 Vicari et al. ................. 585/531

FOREIGN PATENT DOCUMENTS

| GB | 1 471 481 | 4/1977 |
|----|-----------|--------|
| WO | WO 98/23566 | 6/1998 |
| WO | WO 99/25668 | 5/1999 |

OTHER PUBLICATIONS

Kosswig/ Stache :Die Tenside (1993) pp. 118–161.

Commereuc et al. "Aspects Chimiques du Procédé Dimerson de Dimérisation des Oléfines" Revue de L'Institut Francais de Petrole vol. 37 No. 5, (1982) pp. 639–649.

*Primary Examiner*—Johann Richter
*Assistant Examiner*—Elvis O. Price
(74) *Attorney, Agent, or Firm*—Novak Druce & Quigg

(57) ABSTRACT

A process for preparing a $C_{13}$-alcohol mixture comprises a) bringing a butene-containing $C_4$-hydrocarbon stream containing less than 5% by weight, based on the butene fraction, of isobutene into contact with a nickel-containing heterogeneous catalyst at elevated temperature, b) isolating a $C_{12}$-olefin fraction from the reaction mixture, c) hydroformylating the $C_{12}$-olefin fraction by reaction with carbon monoxide and hydrogen in the presence of a cobalt catalyst and d) hydrogenating the product from c).

The alcohol mixture is suitable for preparing surfactants by alkoxylation, glycosidation, sulfation, phosphation, alkoxylation and subsequent sulfation or alkoxylation and subsequent phosphation.

9 Claims, 1 Drawing Sheet

$C_{13}$ ALCOHOL MIXTURE AND FUNCTIONALISED $C_{13}$ ALCOHOL MIXTURE

This application is a 371 of PCT/EP00/11440, filed Nov. 17, 2000.

The present invention relates to a $C_{13}$-alcohol mixture which is suitable, in particular, for the preparation of surfactants. It further relates to a functionalized $C_{13}$-alcohol mixture having surfactant properties.

The use of fatty alcohols having from about 8 to 20 carbon atoms for the preparation of nonionic and anionic surfactants is known. For this purpose, the alcohols are subjected to an appropriate functionalization reaction, e.g. by alkoxylation or glycosidation. The alkoxylates obtained can either be used directly as nonionic surface-active substances or be converted into anionic surface-active substances by another functionalization reaction, for example by sulfation or phosphation. The use properties of these surfactants, e.g. their wetting capability, foam formation, fat-dissolving capability, biodegradability, etc., are determined essentially by the. chain length and the degree of branching of the hydrophobic hydrocarbon radical of the alcohol used. Alcohols which are well suited for further processing to give effective surfactants are also referred to as surfactant alcohols. Kosswig/Stache, "Die Tenside", Carl Hanser Verlag, Munich, Vienna, 1993, Chapters 2.2 and 2.3, describes the reaction of fatty alcohols with alkylene oxides to give the corresponding fatty alcohol alkoxylates and also their sulfation and phosphation.

Fatty alcohols are obtainable both from natural sources and by synthetic routes, e.g. by build up from starting materials having a smaller number of carbon atoms. Thus, for example, the SHOP process (Shell Higher Olefin Process) gives, starting from ethene, olefin fractions having a number of carbon atoms suitable for further processing to produce surfactants. The functionalization of the olefins to form the corresponding alcohols is carried out, for example, by hydroformylation and hydrogenation. A disadvantage of the ethylene-based processes for preparing fatty alcohols is the high cost of the starting material, which adversely affects the economics of these processes.

Olefins having a number of carbon atoms suitable for further processing to give surfactant alcohols can also be obtained by oligomerization of $C_3$–$C_6$-alkenes, in particular propene or butene or mixtures thereof. In the DIMERSOL process (cf. Revue de l'Institut Francais du Petrole, Vol. 37, No. 5, September/October 1982, p. 639 ff), propene or butene are oligomerized in a homogeneous phase in the presence of a catalyst system comprising a transition metal derivative and an organometallic compound. Typical catalyst systems are Ni(O) complexes in combination with Lewis acids such as $AlCl_3$, $BF_3$, $SbF_5$, etc., or Ni(II) complexes in combination with alkylaluminum halides. A disadvantage of this homogeneously catalyzed process is the difficulty of separating the catalyst from the reaction mixture. A further disadvantage is that the higher olefins obtained are always contaminated with traces of halogen which originate from the oligomerization catalyst and are not completely removed when the catalyst is separated off. The residual halogen content causes accelerated corrosion of plant components which come into contact with the product stream. In addition, traces of halogen in the higher olefins impair the activity of the catalysts in the further processing steps, in particular of the hydroformylation and hydrogenation catalysts. The traces of halogen are predominantly present in the form of organic halogen compounds. The presence of such compounds in products which are to be further processed to produce consumer products is fundamentally undesirable.

It is also known that lower olefins can be oligomerized by means of heterogeneous, acidic catalysts, e.g. supported phosphoric acid. However, the use of these heterogeneous, acidic catalysts leads to strongly branched higher olefins, which is disadvantageous.

WO 98/23566 describes a mixture of branched primary alcohols which is obtainable, inter alia, by dimerizing a $C_6$–$C_{10}$-olefin in the presence of a homogeneous dimerization catalyst and then converting the resulting branched $C_{12}$–$C_{20}$-olefin into the mixture of branched primary alcohols.

The use properties of the known surfactant alcohols or the functionalized surfactant alcohols prepared therefrom are not fully satisfactory.

It is an object of the present invention to provide halogen-free surfactant alcohols and surfactants obtained therefrom. The branching structure of the surfactant alcohols should be such that a balanced property spectrum in respect of surface-active properties, environmental toxicity and biodegradability of the surfactants is achieved.

We have found that this object is achieved by a process for preparing a $C_{13}$-alcohol mixture, which comprises a) bringing a butene-containing $C_4$-hydrocarbon stream containing less than 5% by weight, based on the butene fraction, of isobutene into contact with a nickel-containing heterogeneous catalyst at elevated temperature, b) isolating a $C_{12}$-olefin fraction from the reaction mixture, c) hydroformylating the $C_{12}$-olefin fraction by reaction with carbon monoxide and hydrogen in the presence of a cobalt catalyst and d) hydrogenating the product from c).

The invention also relates to a $C_{13}$-alcohol mixture which can be obtained using the above process.

The $C_{13}$-alcohol mixture of the present invention is preferably essentially halogen-free, i.e. it contains less than 3 ppm by weight, in particular less than 1 ppm by weight, of halogen, in particular chlorine.

a) Butene Trimerization

To prepare the $C_{13}$-alcohol mixture, $C_{12}$-olefins are built up from $C_4$ molecules in a first step. For this purpose, butenes are oligomerized in a manner known per se over a nickel-containing heterogeneous catalyst. Depending on the process conditions selected, different relative amounts of butene dimers, trimers and higher oligomers are obtained. For the present purposes, the butene trimers, i.e. $C_{12}$-olefins, are processed further. To achieve the desired degree of branching of the $C_{13}$-alcohol mixture obtained after hydroformylation/hydrogenation, the butenes used have to be predominantly linear, i.e. the isobutene content has to be less than 5% by weight. The butenes can be admixed with saturated $C_4$-hydrocarbons which act as diluent in the oligomerization.

The heterogeneous, nickel-containing catalysts used can have different structures, preference being given to catalysts comprising nickel oxide. Suitable catalysts are those known per se, as are described in C. T. O'Connor et al., Catalysis Today, Vol. 6 (1990), pp. 336–338. In particular, use is made of supported nickel catalysts. The support materials can be, for example, silica, alumina, aluminosilicates, aluminosilicates having sheet structures and zeolites such as mordenite, faujasite, zeolite X, zeolite Y and ZSM-5, zirconium oxide which has been treated with acids or sulfated titanium dioxide. Particularly suitable catalysts are precipitated catalysts which are obtainable by mixing aqueous solutions of nickel salts and silicates, e.g. sodium silicate with nickel nitrate, and possibly aluminum salts such as aluminum nitrate followed by calcination. It is also possible to use catalysts which are obtained by intercalation of $Ni^{2+}$ ions into natural or synthetic sheet silicates such as montmorillonites by ion exchange. Suitable catalysts can also be obtained by impregnation of silica, alumina or aluminosilicates with aqueous solutions of soluble nickel salts such as nickel nitrate, nickel sulfate or nickel chloride, and subsequent calcination.

Particular preference is given to catalysts which consist essentially of NiO, $SiO_2$, $TiO_2$ and/or $ZrO_2$ and, if desired, $Al_2O_3$. Most preferred is a catalyst comprising, as significant active constituents, from 10 to 70% by weight of nickel oxide, from 5 to 30% by weight of titanium dioxide and/or zirconium dioxide, from 0 to 20% by weight of aluminum oxide and silicon dioxide as balance. Such a catalyst is obtainable by precipitation of the catalyst composition at pH 5–9 by addition of an aqueous solution of nickel nitrate to an alkali metal water glass solution containing titanium dioxide and/or zirconium dioxide, filtration, drying and heat treatment at from 350 to 650° C. For the preparation of these catalysts, specific reference may be made to DE-4339713. The full disclosure of this publication and the prior art cited therein is hereby incorporated by reference.

The catalyst is preferably in the form of discrete particles or bodies, e.g. in the form of pellets having, for example, a diameter of from 2 to 6 mm and a height of from 3 to 5 mm, rings having, for example, an external diameter of from 5 to 7 mm, a height of from 2 to 5 mm and a hole diameter of from 2 to 3 mm, or extrudates of various lengths having a diameter of, for example, from 1.5 to 5 mm. Such shapes are obtained in a manner known per se by tableting or extrusion, usually using a tableting aid such as graphite or stearic acid.

The $C_4$-hydrocarbon stream generally comprises from 50 to 100% by weight, preferably from 60 to 90% by weight, of butenes and from 0 to 50% by weight, preferably from 10 to 40% by weight, of butanes. The butene fraction contains less than 5% by weight, in particular less than 3% by weight, of isobutene, based on the butene fraction. The butene fraction generally has the following composition (in each case based on the butene fraction):

| | |
|---|---|
| 1-butene | from 1 to 50% by weight |
| cis-2-butene | from 1 to 50% by weight |
| trans-2-butene | from 1 to 99% by weight |
| isobutene | from 1 to 5% by weight |

A particularly preferred starting material is raffinate II, which is an isobutene-depleted $C_4$ fraction from an FCC plant or a steam cracker.

If diolefins or alkynes are present in the $C_4$-hydrocarbon stream, they are removed from the hydrocarbon stream prior to the oligomerization so as to leave a diolefin/alkyne content of preferably less than 10 ppm by weight, in particular less than 5 ppm by weight, particularly preferably less than 1 ppm by weight. They are preferably removed by selective hydrogenation, e.g. as described in EP-81041 and DE-1568542.

In addition, it is advantageous to largely remove oxygen-containing compounds such as alcohols, aldehydes, ketones or ethers from the olefin-rich hydrocarbon mixture. For this purpose, it is advantageous to pass the $C_4$-hydrocarbon stream over an adsorbent, e.g. molecular sieves, in particular molecular sieves having a pore diameter of from >4 Å to 5 Å. The concentration of oxygen-containing compounds in the $C_4$-hydrocarbon stream is preferably less than 1 ppm by weight, in particular less than 0.5 ppm by weight.

The $C_4$-hydrocarbon stream is preferably brought into contact with the oligomerization catalyst at from 30 to 280° C., in particular from 30 to 140° C. and particularly preferably from 40 to 130° C. This is preferably carried out at a pressure of from 10 to 300 bar, in particular from 15 to 100 bar and particularly preferably from 20 to 80 bar. The pressure is advantageously set so that the $C_4$-hydrocarbon stream is in the liquid or supercritical state at the selected temperature.

The $C_4$-hydrocarbon stream is usually passed over one or more fixed catalyst beds. Suitable, possibly pressure-rated, reaction apparatuses for bringing the hydrocarbon stream into contact with the heterogeneous catalyst are known to those skilled in the art. They include generally customary reactors for gas/solid reactions or liquid/solid reactions. Examples of suitable reactors are shell-and-tube reactors or shaft ovens. Owing to the lower capital costs, shaft ovens are preferred. The oligomerization can be carried out in a single reactor in which the oligomerization catalyst may be present in one or more fixed beds. Alternatively, it is possible to use a reactor cascade comprising two or more, preferably two, reactors connected in series. Such a reactor cascade is operated so that only partial oligomerization of the butenes occurs on passing through the reactor or reactors upstream of the last reactor of the cascade and the desired final conversion is achieved only when the reaction mixture passes through the last reactor of the cascade. In the individual reactors of the reactor cascade, the oligomerization catalyst can be located in one or more catalyst beds. Furthermore, different reaction conditions in respect of pressure and/or temperature within the abovementioned pressure and temperature ranges can be set in the individual reactors of the reactor cascade. In addition, it is possible to use different oligomerization catalysts in the individual reactors of the cascade, although the use of the same catalyst in all reactors of the cascade is preferred. The preferred reactor is generally a vertical cylindrical tube which is charged with the catalyst and through which the olefin-rich hydrocarbon mixture flows, for example, from the top downward.

After leaving the reactor or the last reactor of a cascade, the oligomers formed are separated from the unreacted butenes and butanes in the reaction product. The oligomers formed can be fractionated or purified in a downstream vacuum fractionation step.

It can sometimes be advantageous to recirculate all or part of the reaction product which has been freed of the oligomers formed and consists essentially of unreacted butenes and butanes.

b) Isolation of a $C_{12}$-olefin Fraction

A $C_{12}$-olefin fraction is isolated from the reaction product of the oligomerization reaction in one or more separation steps. Suitable separation apparatuses are the customary apparatuses known to those skilled in the art. They include, for example, distillation columns such as tray columns which may, if desired, be equipped with bubble caps, sieve plates, sieve trays, valves, side offtakes, etc., evaporators such as thin film evaporators, falling film evaporators, wiper blade evaporators, Sambay evaporators, etc., and combinations thereof. The isolation of the $C_{12}$-olefin fraction is preferably carried out by fractional distillation.

The ISO index of the $C_{12}$-olefin fraction, which indicates the mean number of branches, is generally from 1.9 to 2.3, preferably from 2.0 to 2.3. The ISO index can be determined, for example, by hydrogenating a sample of the $C_{12}$-olefin fraction to form the dodecanes and determining the mean number of methyl groups from the $^1$H-NMR spectrum with the aid of the signal area attributable to methyl groups and the signal area attributable to all protons. The ISO index is the mean number of methyl groups minus two.

c) Hydroformylation

To prepare the alcohol mixture of the present invention, the $C_{12}$-olefin fraction which has been isolated is hydroformylated to form $C_{13}$-aldehydes and these are subsequently hydrogenated to form $C_{13}$-alcohols. The preparation of the alcohol mixtures can be carried out in a single step or in two separate reaction steps.

A review of hydroformylation processes and suitable catalysts may be found in Beller et al., Journal of Molecular Catalysis A 104 (1995), pp. 17–85.

For the purposes of the present invention, it is critical that the hydroformylation is carried out in the presence of a cobalt hydroformylation catalyst. The amount of hydroformylation catalyst is generally from 0.001 to 0.5% by weight, calculated as cobalt metal and based on the amount of the olefins to be hydroformylated. The reaction temperature is generally in the range from about 100 to 250° C., preferably from 150 to 210° C. The reaction can be carried out at a superatmospheric pressure of from about 10 to 650 bar. The hydroformylation is preferably carried out in the presence of water, but it can also be carried out in the absence of water.

Carbon monoxide and hydrogen are usually used in the form of a mixture, known as synthesis gas. The composition of the synthesis gas used can vary within a wide range. The molar ratio of carbon monoxide to hydrogen is generally from about 2.5:1 to 1:2.5. A preferred ratio is about 1:1.5.

The hydroformylation-active cobalt catalyst is $HCo(CO)_4$. The catalyst can be preformed outside the hydroformylation reactor, e.g. from a cobalt(II) salt in the presence of synthesis gas, and introduced into the hydroformylation reactor together with the $C_{12}$-olefins and the synthesis gas. Alternatively, the formation of the catalytically active species from catalyst precursors may take place only under the hydroformylation conditions, i.e. in the reaction zone. Suitable catalyst precursors are cobalt(II) salts such as cobalt(II) carboxylates, e.g. cobalt(II) formate or cobalt(II) acetate, and also cobalt(II) acetylacetonate or $CO_2(CO)_8$.

The cobalt catalyst, which is homogeneously dissolved in the reaction medium, can be separated from the hydroformylation product by treating the reaction product of the hydroformylation with oxygen or air in the presence of an acidic aqueous solution. This destroys the cobalt catalyst by oxidation to form cobalt(II) salts. The cobalt(II) salts are water-soluble and are extracted into the aqueous phase which can be separated off and returned to the hydroformylation process.

The hydroformylation can be carried out continuously by, for example, (i) bringing an aqueous cobalt(II) salt solution into intimate contact with hydrogen and carbon monoxide to form a hydroformylation-active cobalt catalyst; (ii) bringing the aqueous phase comprising the cobalt catalyst into intimate contact with the olefins and also hydrogen and carbon monoxide in a reaction zone, so that the cobalt catalyst is extracted into the organic phase and the olefins are hydroformylated; and (iii) treating the output from the reaction zone with oxygen so that the cobalt catalyst is decomposed to form cobalt(II) salts which are back-extracted into the aqueous phase, and separating the phases. The aqueous cobalt(II) salt solution is then recirculated to the process. Suitable cobalt(II) salts are, in particular, cobalt(II) acetate and cobalt(II) formate. The formation of the cobalt catalyst, the extraction of the cobalt catalyst into the organic phase and the hydroformylation of the olefins can advantageously be carried out in one step by bringing the aqueous cobalt(II) salt solution, the olefins and any organic solvent plus hydrogen and carbon monoxide into intimate contact in the reaction zone under hydroformylation conditions, e.g. by means of a mixing nozzle.

The crude aldehydes or aldehyde (alcohol mixtures obtained in the hydroformylation can, if desired, be isolated before hydrogenation by customary methods known to those skilled in the art, and purified if desired.

d) Hydrogenation

For the hydrogenation, the reaction mixtures obtained in the hydroformylation are reacted with hydrogen in the presence of a hydrogenation catalyst.

Suitable hydrogenation catalysts are, in general, transition metals such as Cr, Mo, W, Fe, Rh, Co, Ni, Pd, Pt, Ru, etc., or mixtures thereof, which may be applied to supports such as activated carbon, aluminum oxide, kieselguhr, etc., to increase the activity and stability. To increase the catalytic activity, it is possible to use Fe, Co and preferably Ni as metal sponge having a very high surface area, including these metals in the form of the Raney catalysts. The surfactant alcohols of the present invention are preferably prepared using a Co/Mo catalyst. The hydrogenation of the oxo aldehydes is preferably carried out at elevated temperatures and superatmospheric pressure, depending on the activity of the catalyst. The hydrogenation temperature is preferably from about 80 to 250° C., and the pressure is preferably from about 50 to 350 bar.

The $C_{13}$-alcohol mixture of the present invention can be isolated in pure form from the reaction mixture obtained from the hydrogenation by customary purification methods known to those skilled in the art, in particular by fractional distillation.

The $C_{13}$-alcohol mixture of the present invention preferably has a mean degree of branching of from 2.1 to 2.5, in particular from 2.2 to 2.4. The degree of branching is defined as the number of methyl groups in one molecule of the alcohol minus 1. The mean degree of branching is the statistical mean of the degree of branching of the molecules of a sample. The mean number of methyl groups in the molecules of a sample can easily be determined by $^1$H-NMR spectroscopy. For this purpose, the signal area corresponding to the methyl protons in the $^1$H-NMR spectrum of a sample is divided by three and then divided by the signal area of the methylene protons of the $CH_2$—OH group divided by two.

The present invention also provides a functionalized alcohol mixture obtained by subjecting an above-described $C_{13}$-alcohol mixture to (i) alkoxylation,
(ii) glycosidation,
(iii) sulfation, (iv) phosphation,
(v) alkoxylation and subsequent sulfation, or
(vi) alkoxylation and subsequent phosphation.

The alkoxylation of the alcohol mixtures is carried out by reaction with at least one alkylene oxide. The alkylene oxides are preferably selected from among compounds of the formula I

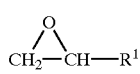

where
R$^1$ is hydrogen or a straight-chain or branched C$_1$–C$_{16}$-alkyl radical,
and mixtures thereof.

The radical R$^1$ in the formula I is preferably a straight-chain or branched C$_1$–C$_8$-alkyl radical, in particular a C$_1$–C$_4$-alkyl radical.

The alkylene oxides are preferably selected from among ethylene oxide, propylene oxide, butylene oxide and mixtures thereof.

The reaction of the alcohol mixtures with the alkylene oxide(s) is carried out by customary methods known to those skilled in the art and in apparatuses customary for this purpose.

The mean chain length of the polyether chains of the alcohol mixtures which have been functionalized in this way can be determined by the molar ratio of alcohol to alkylene oxide. Preference is given to preparing alkoxylated alcohol mixtures having from about 1 to 200, preferably from about 1 to 50, in particular from 1 to 10, alkylene oxide units.

The alcohol mixtures can, if desired, be reacted with only one alkylene oxide or with two or more different alkylene oxides. When the alcohol mixtures are reacted with a mixture of two or more alkylene oxides, the alkylene oxide units in the resulting alkoxylates are distributed essentially randomly. If the alkylene oxides are used separately in succession, this results in alkoxylates which have the alkylene oxide units copolymerized in the form of blocks corresponding to the order of addition.

The alkoxylation can be catalyzed by strong bases such as alkali metal hydroxides and alkaline earth metal hydroxides, Brönsted acids or Lewis acids such as AlCl$_3$, BF$_3$, etc.

The alkoxylation is preferably carried out at from about 80 to 250° C., preferably from about 100 to 220° C. The pressure is preferably in the range from ambient pressure to 600 bar. If desired, the alkylene oxide may be admixed with inert gas, e.g. with from about 5 to 60% of inert gas.

The functionalized alcohol mixtures obtained by alkoxylation display very good surface activity and can advantageously be used as nonionic surfactants in many application areas, e.g. as surfactant, dispersant, paper auxiliary, detergent, corrosion inhibitor, auxiliary for dispersions or encrustation inhibitor.

The glycosidation of the alcohol mixtures is carried out by single, double or multiple reaction of the alcohol mixtures of the present invention with monosaccharides, disaccharides or polysaccharides. The reaction is carried out according to customary methods known to those skilled in the art. These include, for instance, acid-catalyzed reaction accompanied by elimination of water. Suitable acids are, for example, mineral acids such as HCl and H$_2$SO$_4$. This generally gives oligosaccharides having a random chain length distribution. The average degree of oligomerization is preferably from 1 to 3 saccharide units. In a further suitable method, the saccharide can firstly be acetalated by reaction with a low molecular weight C$_1$–C$_8$-alkanol such as ethanol, propanol or butanol. The acetalation is preferably catalyzed by acid. The resulting glycoside of the low molecular weight alcohol can subsequently be reacted with an alcohol mixture according to the present invention to form the corresponding glycosides. Aqueous saccharide solutions are generally suitable for this reaction. In a further suitable process, the saccharide can firstly be converted into the corresponding O-acetylhalosaccharide by reaction with a hydrogen halide and subsequently be glycosidated with an alcohol mixture according to the present invention in the presence of acid-forming compounds.

Preference is given to using monosaccharides for the glycosidation. In particular, hexoses such as glucose, fructose, galactose, mannose, etc., and pentoses such as arabinose, xylose, ribose, etc., are used. Particular preference is given to using glucose. The saccharides can be used individually or in the form of mixtures. Saccharide mixtures generally result in glycosides having randomly distributed sugar groups. Multiple addition of saccharide onto one alcoholic hydroxyl group results in polyglycosides of the alcohol mixtures of the present invention. For the polyglycosidation, too, it is possible to use a plurality of saccharides in succession or as a mixture, so that the saccharides are built into the resulting functionalized alcohol mixtures in the form of blocks or in a random distribution. Depending on the reaction conditions, in particular the reaction temperature, furanose or pyranose structures can result.

Suitable methods and reaction conditions for the glycosidation are described, for example, in Ullmann's Encyclopedia of Industrial Chemistry, 5th Edition, Vol. A25 (1994), pp. 792–793 and the documents cited therein.

The functionalized alcohol mixtures obtained by glycosidation display very good surface activity and can advantageously be used as nonionic surfactants in many application areas.

The sulfation or phosphation of the above-described alcohol mixtures or alkoxylated alcohol mixtures is carried out by reaction with sulfuric acid or sulfuric acid derivatives to form acid alkyl sulfates or alkyl ether sulfates or by reaction with phosphoric acid or phosphoric acid derivatives to give acid alkyl phosphates or alkyl ether phosphates.

Suitable methods for the sulfation of alcohols are the customary methods known to those skilled in the art, as are described, for example, in U.S. Pat. No. 3,462,525, U.S. Pat. No. 3,420,875 or U.S. Pat. No. 3,524,864, which are hereby fully incorporated by reference. Suitable methods of sulfation are also described in Ullmann's Encyclopedia of Industrial Chemistry, 5th Edition, Vol. A25 (1994), pp. 779–783 and the literature cited therein.

If sulfuric acid is used for the sulfation of the alcohol mixtures of the present invention, it preferably has a concentration of from 75 to 100% by weight, in particular from 85 to 98% by weight. Such sulfuric acid is obtainable under the names concentrated sulfuric acid and monohydrate.

If desired, a solvent or diluent can be used in the sulfation with sulfuric acid. Suitable solvents are, for example, ones which form an azeotrope with water, e.g. toluene.

In a preferred embodiment for preparing sulfated alcohol mixtures, the alcohol mixture is placed in a reaction vessel and the sulfating agent is added with continual mixing. To achieve essentially complete esterification of the alcohol mixture, the molar ratio of alkanol to sulfating agent is preferably from about 1:1 to 1:1.5, in particular from 1:1 to 1:1.2. If desired, the sulfating agent can also be used in a molar deficiency, e.g. in the sulfation of alkoxylated alcohol mixtures when mixtures of nonionic and anionic surface-active compounds are to be prepared. The sulfation is preferably carried out at a temperature in the range from ambient temperature to 80° C., in particular from 40 to 75° C.

Further suitable sulfating agents are, for example, sulfur trioxide, sulfur trioxide complexes, solutions of sulfur trioxide in sulfuric acid (oleum), chlorosulfonic acid, sulfuryl chloride, amidosulfonic acid, etc. When using sulfur trioxide as sulfating agent, the reaction can advantageously be carried out in a falling film evaporator, preferably in countercurrent. The reaction can be carried out batchwise or continuously.

The reaction mixtures obtained in the sulfation are worked up by customary methods known to those skilled in the art. These include, for example, neutralization, removal of any solvents used, etc.

The phosphation of the above-described alcohol mixtures and alkoxylated alcohol mixtures is generally carried out in a manner analogous to the sulfation.

Suitable methods for the phosphation of alcohols are the customary methods known to those skilled in the art, as are described, for example, in Synthesis 1985, pp. 449–488, which is hereby fully incorporated by reference.

Suitable phosphating agents are, for example, phosphoric acid, polyphosphoric acid, phosphorus pentoxide, $POCl_3$, etc. When using $POCl_3$, the remaining acid chloride functions are hydrolyzed after the esterification.

The present invention further provides for the use of the functionalized alcohol mixtures as surfactants, dispersants, paper auxiliaries, detergents, corrosion inhibitors, auxiliaries for dispersions, and encrustation inhibitors.

The invention is illustrated by the nonlimiting examples below.

EXAMPLE 1

In an isothermally operated reactor having a length of about 1.5 m and a diameter of 30 mm, raffinate II having the following composition was reacted at 20 bar and 80° C. over a heterogeneous catalyst.

| | |
|---|---|
| i-butane: | 3% by weight |
| n-butane: | 15% by weight |
| i-butene: | 2% by weight |
| 1-butene: | 30% by weight |
| trans-2-butene: | 32% by weight |
| cis-2-butene: | 18% by weight |

The catalyst employed was a material which had been produced as 5 described in DE-4339713 in the form of pellets (5 mm×5 mm). The composition in % by weight of the active components was: 50% by weight of NiO, 12.5% by weight of $TiO_2$, 33.5% by weight of $SiO_2$, 4% by weight of $Al_2O_3$. The throughput was 0.75 kg of raffinate II/(l of cat×h). The reaction was carried out without recirculation of $C_4$-hydrocarbons. The $C_4$ conversion, based on the butenes present in the raffinate II, was 52.0% by weight. The selectivity in % by weight was as follows: $C_8$: 76.9; $C_{12}$: 18.4 and $C_{16+}$: 4.7. The $C_{12}$-olefin fraction was isolated from the resulting reaction mixture by fractional distillation.

To characterize the $C_{12}$-olefin fraction, A sample was hydrogenated with $H_2$ in the presence of Pd/C. According to $^1$H-NMR spectroscopy, the $C_{12}$-paraffin fraction obtained has an average of 4.13 methyl groups per molecule, corresponding to an ISO index of 2.13.

EXAMPLE 2

Preparation of tridecanol mixtures according to the present invention by hydroformylation, hydrogenation and distillation of the dodecene mixtures.

750 g of the dodecene mixture prepared as described in Example 1 were hydroformylated for five hours in an autoclave fitted with a reciprocating stirrer using 0.13% by weight of cobalt as $Co_2(CO)_8$ with addition of 75 g of water at 185° C. and under a synthesis gas pressure of 280 bar with a volume mixing ratio of $H_2$ to CO of 60:40; the consumption of synthesis gas, recognizable by a drop in the pressure in the autoclave, was made up by injection of further synthesis gas. After depressurizing the autoclave, the cobalt was removed from the reaction product by addition of 10% strength by weight aqueous acetic acid and passing air through the mixture and the organic product phase was hydrogenated for 10 hours at 125° C. and a hydrogen pressure of 280 bar using 50 g of Raney nickel. The tridecanol fraction was separated from the $C_{12}$-paraffins and from high boilers by fractional distillation of the reaction product.

The OH number of the tridecanol was 278 mg KOH/g. $^1$H-NMR spectroscopy indicated 3.27 methyl groups/molecule, corresponding to a degree of branching of 2.27.

Figure 1:
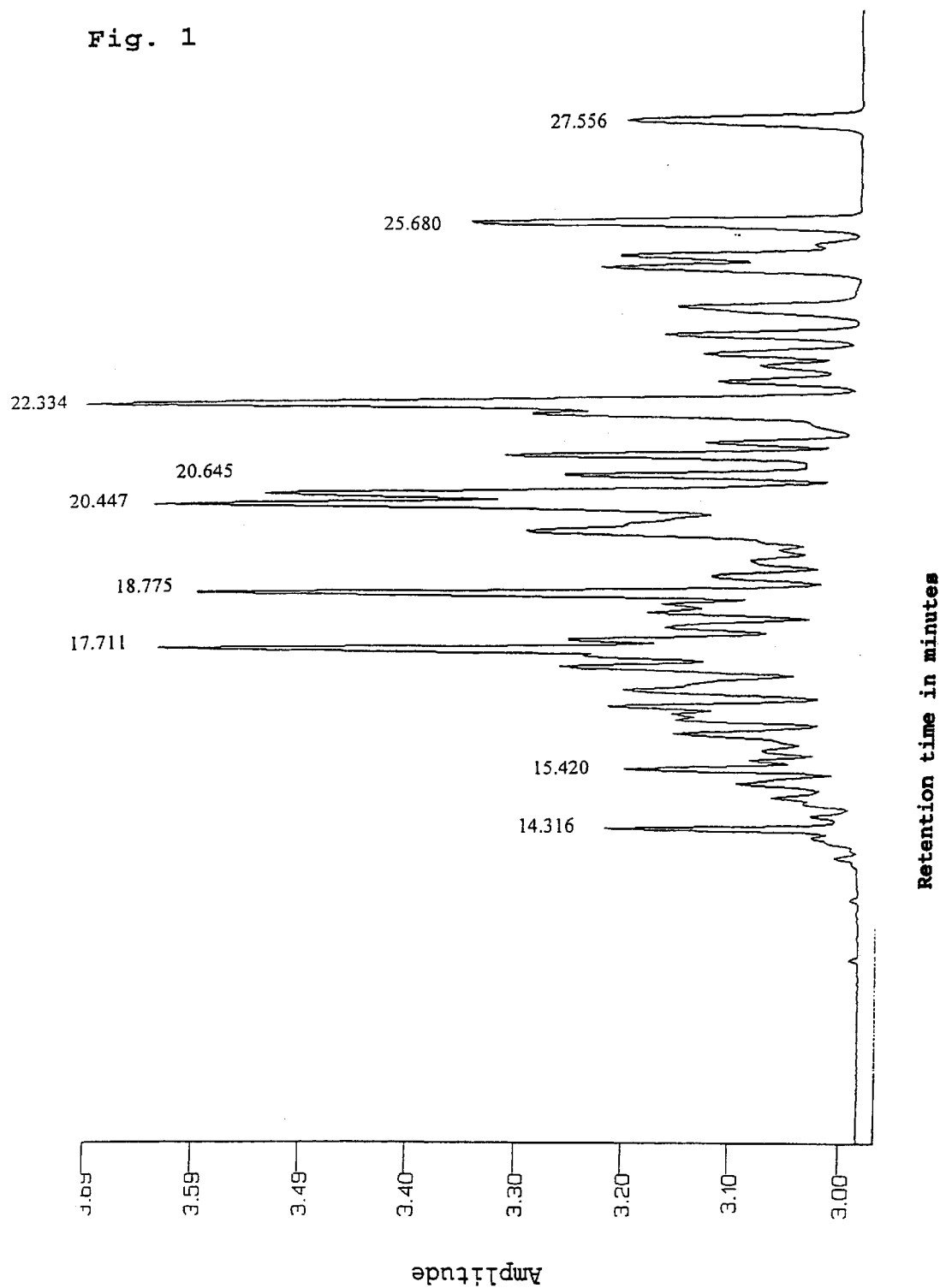
FIG. 1 shows a gas chromatogram of the tridecanol (as trimethylsilyl ether), which was measured under the following conditions.

Sample preparation: 3 drops of tridecanol were reacted with 1.5 ml of N-methyltrimethylsilyltrifluoroacetamide for 60 minutes at 80° C. The injection volume was 1 $\mu$l.

Separation conditions: Column: Ultra-1 Hewlett Packard; length: 50 m, internal diameter: 0.33 mm, film thickness: 0.2 $\mu$m; prepressure: 200 mPa; split: 88 ml/min; temperature: 160° C. (isothermal); injector temperature: 250° C.; detector temperature: 300° C.; detection: FID.

EXAMPLE 3

Preparation of a Fatty Alcohol Ethoxylate Containing 7 mol of Ethylene Oxide 400 g of tridecanol (prepared as described in Example 2) were introduced together with 1.5 g of NaOH into a dry 2 l autoclave. The contents of the autoclave were heated to 150° C. and 616 g of ethylene oxide were injected in the autoclave under pressure. After all the ethylene oxide was in the autoclave, the autoclave was held at 150° C. for 30 minutes. After cooling, the catalyst was neutralized with sulfuric acid.

The surfactant obtained has a cloud point of 73° C., measured at a concentration of 1% in 10% strength butyl diglycol solution in accordance with DIN 53 917. The surface tension at a concentration of 1 g/l is 27.8 mN/m, measured in accordance with DIN 53 914.

EXAMPLE 4

Preparation of a Fatty Alcohol Ethoxylate Containing 3 mol of Ethylene Oxide 600 g of tridecanol (prepared as described in Example 2) were introduced together with 1.5 g of NaOH into a dry 2 l autoclave. The contents of the autoclave were heated to 150° C. and 396 g of ethylene oxide were injected in the autoclave under pressure. After all the ethylene oxide was in the autoclave, the autoclave was held at 150° C. for 30 minutes. After cooling, the catalyst was neutralized with sulfuric acid.

The surfactant obtained has a cloud point of 45.5° C., measured at a concentration of 1% in 10% strength butyl diglycol solution in accordance with DIN 53 917. The surface tension at a concentration of 1 g/l is 27.1 mN/m, measured in accordance with DIN 53 914.

EXAMPLE 5

Preparation of an Alkyl Phosphate 300 g of tridecanol (prepared as described in Example 2) were heated to 60° C. under nitrogen in a stirred vessel and 125 g of polyphosphoric acid were added slowly, with care being taken to ensure that the temperature did not exceed 65° C. Toward the end of the addition, the temperature was increased to 70° C. and the mixture was stirred for one hour at this temperature.

The surface tension of the resulting alkyl phosphate at a concentration of 1 g/l is 32.3 mN/m, measured in accordance with DIN 53 914.

EXAMPLE 6

Preparation of an Alkyl Ether Phosphate 560 g of the fatty alcohol ethoxylate prepared in Example 2 were heated to 60° C. under nitrogen in a stirred vessel and 92 g of polyphosphoric acid were added slowly, with care being taken to ensure that the temperature did not exceed 65° C. Toward the end of the addition, the temperature was increased to 70° C. and the mixture was stirred for one hour at this temperature.

The surface tension of the resulting alkyl ether phosphate at a concentration of 1 g/l is 30.8 mN/m, measured in accordance with DIN 53 914.

We claim:

1. A process for preparing a $C_{13}$-alcohol mixture, which comprises
   a) bringing a butene-containing $C_4$-hydrocarbon stream containing less than 5% by weight, based on the butene fraction, of isobutene into contact with a nickel-containing heterogeneous catalyst at elevated temperature,
   b) isolating a $C_{12}$-olefin fraction from the reaction mixture,
   c) hydroformylating the $C_{12}$-olefin fraction by reaction with carbon monoxide and hydrogen in the presence of a cobalt catalyst and
   d) hydrogenating the product from c).

2. A process as claimed in claim 1, wherein the $C_{12}$-olefin fraction has an ISO index of from 1.9 to 2.3.

3. A process as claimed in claim 1, wherein the butene-containing $C_4$-hydrocarbon stream comprises from 60 to 90% by weight of butenes and from 10 to 40% by. weight of butanes.

4. A process as claimed in claim 1, wherein the nickel-containing heterogeneous catalyst comprises nickel oxide.

5. A process as claimed in claim 4, wherein the catalyst consists essentially of NiO, $SiO_2$, $TiO_2$ and/or $ZrO_2$ and, if desired, $Al_2O_3$.

6. A $C_{13}$-alcohol mixture obtained by
   a) bringing a butene-carrying $C_4$-hydrocarbon stream containing less than 5% by weight, based on the butene fraction, of isobutene into contact with a nickel-containing heterogeneous catalyst at elevated temperature,
   b) isolating a $C_{12}$-olefin fraction from the reaction mixture,
   c) hydroformylating the $C_{12}$-olefin fraction by reaction with carbon monoxide and hydrogen in the presence of a cobalt catalyst and
   d) hydrogenating the product from c).

7. A $C_{13}$-alcohol mixture as claimed in claim 6 which has a degree of branching in the range from 2.2 to 2.5.

8. A functionalized alcohol mixture obtained by subjecting a $C_{13}$-alcohol mixture as claimed in claim 6 to alkoxylation, glycosidation, sulfation, phosphation, alkoxylation and subsequent sulfation or alkoxylation and subsequent phosphation.

9. A surfactant, dispersant, paper auxiliary, detergent, corrosion inhibitor, auxiliary for dispersions or encrustation inhibitor comprising the functionalized alcohol mixture as claimed in claim 8.

\* \* \* \* \*